(12) United States Patent
Kobayashi et al.

(10) Patent No.: US 7,705,161 B2
(45) Date of Patent: Apr. 27, 2010

(54) PROCESS FOR PRODUCING NITROGENOUS 5-MEMBERED CYCLIC COMPOUND

(75) Inventors: Shu Kobayashi, Tokyo (JP); Yasuhiro Yamashita, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 761 days.

(21) Appl. No.: 10/592,139

(22) PCT Filed: Feb. 21, 2005

(86) PCT No.: PCT/JP2005/003236

§ 371 (c)(1),
(2), (4) Date: Nov. 8, 2006

(87) PCT Pub. No.: WO2005/085204

PCT Pub. Date: Sep. 15, 2005

(65) Prior Publication Data

US 2007/0191614 A1    Aug. 16, 2007

(30) Foreign Application Priority Data

Mar. 9, 2004    (JP)    ............... 2004-066434

(51) Int. Cl.
*C07D 231/06*    (2006.01)
(52) U.S. Cl. .................................. 548/379.4
(58) Field of Classification Search ............ None
See application file for complete search history.

(56) References Cited

U.S. PATENT DOCUMENTS 6,417,368 B1    7/2002    Kobayashi et al.

FOREIGN PATENT DOCUMENTS

JP    11-217362    8/1999
JP    11-263758    9/1999

OTHER PUBLICATIONS

Shu Kobayashi et al., "Asymmetric Intramolecular [3+2] Cycloaddition Reactions of Acylhydrazones/Olefins Using a Chiral Zirconium Catalyst", J. Am. Chem. Soc., 124, pp. 13678-13679, 2002.
Shu Kobayashi et al., "Lewis acid-mediated [3+2] cycloaddition between hydrazones and olefins", Tetrahedron Letters, 44, pp. 3351-3354, 2003.
Yasuhiro Yamashita et al., "Zirconium-Catalyzed Enantioselective [3+2] Cycloaddition of Hydrazones to Olefins Leading to Optically Active Pyrazolidine, Pyrazoline, and 1,3-Diamine Derivatives", J. Am. Chem. Soc., 126, pp. 11279-11282, 2004.
Hidekazu Oyamada et al., "Rare Earth Triflate-Catalyzed Addition Reactions of Acylhydrazones with Silyl Enolates. A Facile Synthesis of Pyrazolone Derivatives", Synlett, pp. 249-250, Mar., 1998.
Davood Azarifar et al., "Synthesis and Characterization of New 3,5-Dinaphthyl Substituted 2-Pyrazolines and Study of Their Antimicrobial Activity", Molecules, 7, pp. 885-895, 2002.

*Primary Examiner*—Kamal A Saeed
(74) *Attorney, Agent, or Firm*—Wenderoth, Lind & Ponack, L.L.P.

(57) ABSTRACT

A method of the intramolecular and intermolecular cyclization of an N-acylhydrazone for obtaining a pyrazoline skeleton or pyrazolidine skeleton under ordinary conditions with high stereoselectivity and in high yield. An N-acylhydrazone represented by the following formula (I): (wherein $R_1$ and $R_2$ are the same or different and each represents hydrogen or a hydrocarbon group and Ar represents an optionally substituted aromatic hydrocarbon group) is converted to an N-acylpyrazoline derivative with high stereoselectivity in the presence of a Lewis acid catalyst or asymmetric Lewis acid catalyst.

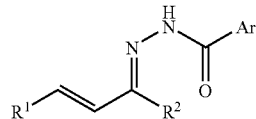

(I)

4 Claims, No Drawings

PROCESS FOR PRODUCING NITROGENOUS 5-MEMBERED CYCLIC COMPOUND

TECHNICAL FIELD

The invention of the present application relates to a process for producing nitrogenous 5-membered cyclic compound. In particular, the invention of the present application relates to a process for the reactions of intramolecular cyclization of an N-acylhydrazone using a Lewis acid catalyst, asymmetric intramolecular cyclization of an N-acylhydrazone using an asymmetric Lewis acid catalyst and intermolecular cyclization of an N-acylhydrazone with an olefinic compound using an asymmetric Lewis acid catalyst.

BACKGROUND ART

In nature, there are a lot of compounds containing a nitrogen atom(s). It has been considered that many 5-membered cyclic skeletons containing a nitrogen atom(s) among these compounds significantly contribute to exhibition of molecular functions. In particular, the compounds having a pyrazoline or pyrazolidine skeleton exhibit various biological activities, and these compounds are recently attracting attention as target chemical structures in the field of medicines, agrichemical, perfumes and the like. On the other hand, a lot of natural substances, for example proteins, are optically active compounds, and it has been known that they exhibit a specific biological activity according to their stereochemistry.

A useful process for preparing nitrogenous 5-membered cyclic skeletons is a [3+2] cyclization reaction. In particular, cyclization reactions using highly reactive 1,3-dipolar compounds such as nitrone have been widely studied. It has already been reported that optically active nitrogenous 5-membered cyclic skeletons are produced by catalytic asymmetric cyclization reactions (for example, Non-Patent Documents 1 and 2). These reactions, however, must be performed under strong acidic condition or heating conditions. It has not been known yet that cyclization reactions for preparing optically active 5-membered cyclic compounds having vicinal nitrogen atoms such as a pyrazoline or pyrazolidine skeleton can be achieved using a catalytic amount of a Lewis acid under a mild condition (for example, Non-Patent Documents 3 and 4).

The inventors of the present application have reported that the intramolecular cyclization reaction of a hydrazone can be achieved using a catalytic amount of zirconium triflate under a mild condition to afford a desired compound with high diastereoselectivity and in high yield (Non-Patent Document 5). However, application of this reaction is limited to some compounds, and the reaction is not versatile.

Non-Patent Document 1: Comprehensive Organic Synthesis; Trost, B. M. Ed.; Pergamon Press: Oxford, 1991: Vol. 5, Chap 3. 3.

Non-Patent Document 2: Gothelf, K. V.; Jorgensen, K. A. Chem. Rev. 1998, 98, 86

Non-Patent Document 3: Kanemasa, S.; Kanai, K. J. Am. Chem. Soc. 2000, 122, 10710;

Non-Patent Document 4: Shintani, R.; Fu, G, C. J. Am. Chem. Soc. 2003, 125, 10778.

Non-Patent Document 5: Kobayashi, S.; Hirabayashi, R.; Shimizu, H.; Ishitani, H.: Yamashita, Y.; Tetrahedron Lett., 2003, 44, 3351.

Non-Patent Document 6: Cox, P. J.; Wang, W.; Snieckus, V. Tetrahedron Lett. 1992, 33, 2253.

Non-Patent Document 7: Yamashita, Y.; Ishitani, H.; Shimizu, H.; Kobayashi, S. J. Am. Chem. Soc. 2002, 124, 3292.

Non-Patent Document 8: Kaya, R.; Beller, N. R. J. Org. Chem. 1981, 46, 196.

DISCLOSURE OF INVENTION

In view of the above situation, the invention of the present application overcomes the limitation of the conventional art. An object of the present invention is to provide a process for producing nitrogenous 5-membered cyclic compound, wherein the reaction can be performed under a normal condition, to afford a pyrazoline or pyrazolidine skeleton with stereoselectivity and in high yield.

The invention of the present application solves the object mentioned above. The invention of the present application provides firstly a process for a reaction of intramolecular cyclization of an N-acylhydrazone characterized in that an N-acylhydrazone represented by the following formula (I)

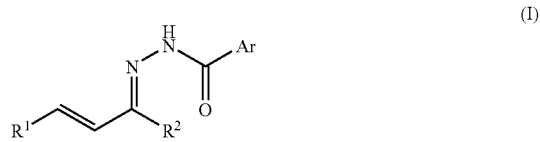

(wherein $R^1$ and $R^2$ are the same or different and each represents a hydrogen atom or a hydrocarbon group, and Ar represents an optionally substituted aromatic hydrocarbon group) is subjected to a reaction with a Lewis acid catalyst to obtain an N-acylpyrazoline derivative represented by the following formula (II)

(wherein $R^1$, $R^2$ and Ar have the same meanings as those indicated above).

The invention of the present application provides secondly a process for a reaction of intramolecular cyclization of an N-acylhydrazone characterized in that a Lewis acid catalyst is scandium triflate.

The invention of the present application thirdly provides a process for a reaction of asymmetric intramolecular cyclization of an N-acylhydrazone represented by the following formula (I)

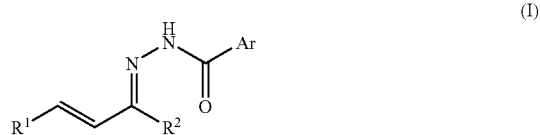

(wherein $R^1$ and $R^2$ are the same or different and each represents a hydrogen atom or a hydrocarbon group, and Ar represents an optionally substituted aromatic hydrocarbon group) characterized in that an N-acylhydrazone (I) is subjected to a reaction with an asymmetric Lewis acid catalyst, which can be obtained by mixing a zirconium alkoxide or zirconium dialkoxide dihalide represented by the following formula (III)

$$ZrP_2Q_2 \quad (III)$$

(wherein P represents an alkoxy group, and Q represents an alkoxy group or a halogen atom) and a binaphthol derivative represented by the following formula (IV)

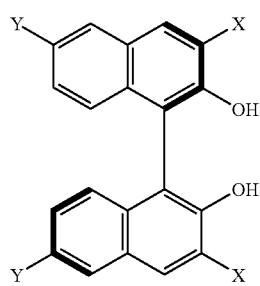

(IV)

(wherein X represents a hydrogen atom, a halogen atom, a hydrocarbon group or a perfluoroalkyl group; Y represents a hydrogen atom, a halogen atom, a hydrocarbon group or a perfluoroalkyl group; and X and Y may be the same.), to afford an optically active N-acylpyrazoline derivative represented by the following formula (II')

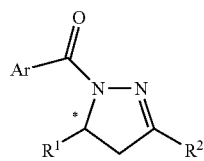

(II')

(wherein $R^1$, $R^2$ and Ar have the same meanings as those indicated above).

Fourthly, the invention of the present application provides a process for a reaction of asymmetric intermolecular cyclization of an N-acylhydrazone represented by the following formula (V)

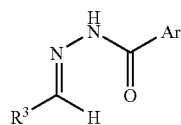

(V)

(wherein $R^3$ represents an optionally substituted hydrocarbon group and Ar represents an optionally substituted aromatic hydrocarbon group) characterized in that N-acylhydrazone (V) is subjected to a reaction with an olefinic compound represented by the following formula (VI)

(VI)

(wherein $R^4$ and $R^5$ are the same or different and each represents a hydrogen atom or a substituent group selected from the group consisting of hydrocarbon, alkoxy and alkylthio; and at least one of $R^4$ and $R^5$ is other than a hydrogen atom) in the presence of an asymmetric Lewis acid catalyst, which can be prepared by mixing a zirconium alkoxide or zirconium dialkoxide dihalide represented by the following formula (III)

$$ZrP_2Q_2 \quad (III)$$

(wherein P represents an alkoxy group and Q represents an alkoxy group or a halogen atom) and a binaphthol derivative represented by the following formula (IV)

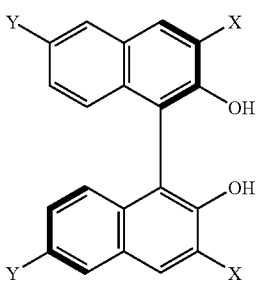

(IV)

(wherein X represents a hydrogen atom, a halogen atom, a hydrocarbon group or a perfluoroalkyl group; Y represents a hydrogen atom, a halogen atom, a hydrocarbon group or a perfluoroalkyl group; and X and Y may be the same.), to obtain an optically active N-acylpyrazolidine derivative represented by the following formula (VII)

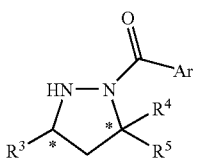

(VII)

(wherein $R^3$ to $R^5$ and Ar have the same meanings as those indicated above).

BEST MODE FOR CARRYING OUT THE INVENTION

The inventors of the present application have found that the [3+2] cyclization reaction of a hydrazone having a specific chemical structure efficiently proceeds by using a catalytic amount of zirconium triflate even under a mild condition such as at room temperature or in an organic solvent. The inventors have continued earnestly to study intramolecular cyclization reactions, asymmetric intramolecular cyclization reactions and asymmetric intermolecular cyclization of various N-acyl-hydrazone derivatives and have completed the present invention.

In a process for a reaction of intramolecular cyclization of the invention of the present application, a cyclization reaction of an N-acylhydrazone having the following formula (I)

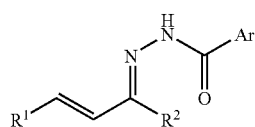
(I)

takes place through use of a Lewis acid catalyst to afford an N-acylpyrazoline derivative having the following formula (II).

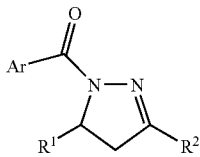
(II)

On the other hand, an asymmetric intramolecular cyclization reaction of an N-acylhydrazone of formula (I) takes place through use of an asymmetric Lewis acid catalyst to give an optically active N-acylpyrazoline derivative having the following formula (II').

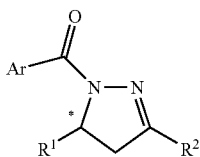
(II')

$R^1$ $R^2$ of an N-acylhydrazone of formula (I), which is a starting material, are the same or different and each represents a hydrogen atom or a hydrocarbon group, and Ar represents an optionally substituted aromatic hydrocarbon group. $R^1$ and $R^2$ are specifically a hydrogen atom or a substituent group selected from saturated aliphatic hydrocarbon, unsaturated aliphatic hydrocarbon and aromatic hydrocarbon. They are preferably a straight or branched chain alkyl group such as methyl, ethyl, n-propyl, i-propyl, n-butyl, sec-butyl, tert-butyl and the like or an aryl group such as phenyl, tolyl, naphthyl and the like. These hydrocarbon groups may optionally have various permissible substituents which do not inhibit the cyclization reaction. On the other hand, Ar is an aryl group such as phenyl, tolyl, naphthyl and the like, which may optionally have a substituent group(s) such as alkyl, amino, nitro, hydroxyl and the like.

Besides, $R^1$, $R^2$ and Ar in formula (II) and (II') have the same meanings as those indicated in the formula (I). That is, in a process for a reaction of an intramolecular cyclization or asymmetric intramolecular cyclization of the invention of the present application, $R^1$, $R^2$ and Ar in formula (I) are left in the products obtained through the cyclization reactions. The groups can appropriately be chosen according to the structure of a target nitrogenous 5-membered cyclic compound.

Various Lewis acids are applicable as a Lewis acid catalyst which can be used for an intramolecular cyclization reaction of an N-acylhydrazone in the invention of the present application. Such examples are rare earth metal triflates, or specifically and preferably, scandium triflate.

On the other hand, an asymmetric Lewis acid catalyst, which can be used for an asymmetric intramolecular cyclization reaction of an N-acylhydrazone, can be obtained by mixing a zirconium alkoxide or zirconium dialkoxide dihaide of the following formula (III)

$$ZrP_2Q_2 \qquad (III)$$

(wherein P represents an alkoxy group and Q represents an alkoxy group or a halogen atom) and a binaphthol derivative of the following formula (IV).

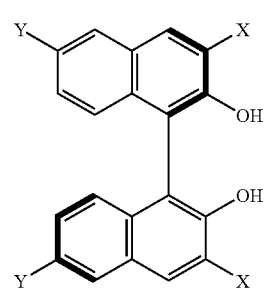
(IV)

Such an asymmetric Lewis acid catalyst can be isolated after mixing zirconiumalkoxide (or zirconium dialkoxide dihalide) and a binaphthol derivative; however, such a catalyst can also be used without isolation and a cyclization reaction can be conducted in a solution system containing the mixture in situ. In formula (IV) of a binaphthol derivative X represents a hydrogen atom, a halogen atom, a hydrocarbon group or a perfluoroalkyl group and Y represents a hydrogen atom, a halogen atom, a hydrocarbon group or a perfluoroalkyl group; and X and Y may be the same. An intramolecular cyclization reaction of an N-acylhydrazone takes place stereoselectively through use of such an asymmetric Lewis acid catalyst.

There are no particular limitations of reaction conditions in intramolecular and asymmetric intramolecular cyclization other than a catalyst, but the cyclization reactions can preferably be performed in an organic solvent such as dichloromethane, benzene, toluene and the like.

The invention of the present application further provides an asymmetric intermolecular cyclization reaction of an N-acylhydrazone represented by the following formula (V).

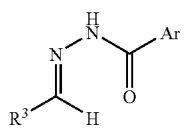
(V)

In such an asymmetric intermolecular cyclization reaction, an N-acylhydrazone of formula (V) is subjected to a reaction with an olefinic compound represented by the following formula (VI)

in the presence of an asymmetric Lewis acid catalyst indicated above, which can be prepared by mixing zirconium alkoxide or zirconium dialkoxide dihalide of formula (III) and a binaphthol derivative of formula (IV) and an asymmetric intermolecular cyclization reaction takes place to give an optically active N-acylpyrazolidine derivative represented by the following formula (VII).

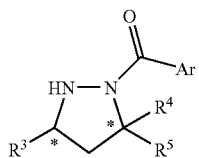

In formula (V), $R^3$ represents an optionally substituted hydrocarbon group, and Ar represents an optionally substituted aromatic hydrocarbon group. $R^3$ is specifically a straight or branched chain alkyl group such as methyl, ethyl, propyl, butyl, pentyl, hexyl and the like; a cyclic alkyl group such as cyclopentyl, cyclohexyl and the like; an aromatic group such as phenyl, tolyl, naphthyl and the like; and a benzyl group, a phenylthiomethyl group and the like. These hydrocarbon groups may optionally have substituent group(s) such as alkoxy, alkylthio, silyloxy, nitro, cyano and the like. Ar is, for example, a phenyl, tolyl, naphthyl, p-nitrophenyl, o,p-dinitrophenyl, aminophenyl group and the like.

On the other hand, in formula (VI), $R^4$ and $R^5$ are the same or different and each represents a hydrogen atom or a substituent group selected from the group consisting of hydrocarbon, alkoxy and alkylthio and at least one of $R^4$ and $R^5$ is other than a hydrogen atom.

In a process for a reaction of asymmetric intermolecular cyclization in the invention of the present application, these substituents of $R^3$ to $R^5$ and Ar are left in the product obtained through an asymmetric intermolecular cyclization reaction. The substituents can appropriately be chosen according to the structure of a target nitrogenous 5-membered cyclic compound.

In a process for a reaction of asymmetric intermolecular cyclization of the invention of the present application, an N-acylhydrazone derivative is subjected to a reaction with an olefinic compound in the presence of a catalytic system as mentioned above, and there are no particular limitations of reaction conditions. However, when a primary alcohol exists in a cyclization reaction system, the stereoselectivity of this reaction increases and the presence of a primary alcohol in a cyclization reaction mixture is preferable. Any kind of primary alcohols can be added and there is no limitation of the amount of a primary alcohol. For example, n-propanol can be used and the amount of n-propanol can be from one to ten equivalents to a binaphthol derivative (IV) indicated above.

Other reaction conditions of an asymmetric intermolecular cyclization of the invention of the present application are not particularly limited. A process for a reaction of asymmetric intermolecular cyclization in the present invention is characterized in that it can be conducted even under very mild condition such as from 0° C. to near room temperature to give a product with high stereoselectivity and in high yield. Various kinds of solvents can be used for cyclization and, for example, dichloromethane, chloroform, benzene, toluene and the like are preferable. As described above, addition of a primary alcohol to a solvent of cyclization is preferable because stereoselectivity in intermolecular cyclization increases.

The N-acylpyrazoline derivatives and N-acylpyrazolidine derivatives which are prepared according to the process of the invention of the present application can be reacted and converted into some desired compounds by an organic synthetic procedure(s). For example, cleavage of the nitrogen and nitrogen bond of these compounds leads to an optically active 1,3-diamine derivative. After an intramolecular cyclization reaction, asymmetric intramolecular cyclization reaction or asymmetric intermolecular cyclization reaction is performed according to the invention of the present application, a crude product can be purified by a general procedure such as extraction, separation, filtration, recrystallization, washing, drying and the like.

Examples of the present invention are explained in detail by the following examples. The examples are not intended to limit the scope of the invention in any way. Various aspects regarding the details are possible.

EXAMPLES

In the following Examples, $^1$H NMR and $^{13}$C NMR were measured, unless otherwise noted, using a JEOL JNM-LA300, JNM-LA400 or JNM-LA500 spectrometer with $CDCL_3$ as solvent. In the spectra of $^1$H NMR, tetrametylsilane was used as an internal standard (0 ppm) and in the spectra of $^{13}$C NMR, $CDCl_3$ was used as an internal standard (77.0 ppm).

Optical rotations were measured using a JASCO P-1010 polarized light spectrometer.

A SHIMADZU LC-10AT (liquid chromatograph), a SHIMADZU SPD-10A (UV detector) and a SHIMADZU C-R6A chromato pack were used for high speed liquid chromatography.

EI high resolution mass spectra (EI-HRMS) were measured using a JEOL-JMX-SX-102 mass spectrometer.

For column chromatography, silica gel 60 (Merk) or aluminum oxide (activated, about 300 mesh) was used. Wacogel B-5F was used for thin layer chromatography.

The solvents used in reactions were dried over MS 4A.

Zirconium propoxide-propanol complex ($Zr(OPr)_4$) was purchased from Fluka Chemie AG and used. Propanol was distilled in the presence of magnesium propoxide. BINOL was prepared by the method described in Non-Patent Documents 6 and 7.

Ketene dimethyl dithioacetal (compound 2a) was synthesized according to the procedure described in Non-Patent Document 8.

Vinyl ether was purchased from Sigma-Aldrich Co. and was distilled just before its use.

All hydrazone compounds were prepared by mixing an appropriate aldehyde and a hydrazine in DMF or THF in the presence of a small amount of aqueous solution of hydrogen chloride at room temperature and purification of the product by recrystallization.

All reactions are conducted under an atmosphere of argon and glass apparatus well dried were used.

Example 1

Intramolecular Cyclization Reaction of N-acylhydrazone

An intramolecular cyclization reaction of N-acylhydrazone obtained from α,β-unsaturated ketone was conducted according to the following reaction formula (A).

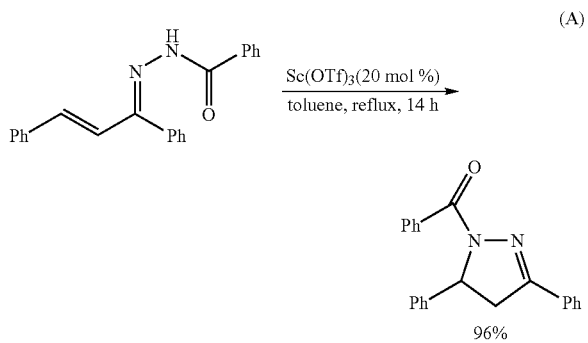

(A)

Under an atmosphere of argon, a suspension of benzoylhydrazone derived from chalcone (compound a, 133 mg) and scandium triflate (40 mg) in toluene (2 ml) was heated under reflux for 14 hours. After cooling the reaction mixture to room temperature, the reaction was stopped by the addition of saturated aqueous solution of sodium hydrogen carbonate to the reaction mixture. The resulting mixture was separated. The water layer was extracted with methylene chloride.

The organic layers were collected. The organic layer was dried over anhydrous sodium sulfate, filtered and concentrated to afford a crude product. It was purified through silica gel thin layer chromatography to give 1-benzoyl-3,5-diphenyl-2-pyrazoline (128 mg, yield 96%) as a target product.

The data for identification of the product is shown in Table 1

TABLE 1

1-Benzoyl-3,5-diphenyl-2-pyrazoline
$^1$H NMR(CDCl$_3$) δ=3.18(dd, 1H, J=17.6, 5.1 Hz), 3.75(dd, 1H, J=17.6, 12.0 Hz), 5.80(dd, 1H, J=11.7, 4.9 Hz), 7.2-7.5(m, 11H), 7.70(m, 2H), 8.03(d, 2H, J=7.1 Hz);
$^{13}$C NMR(CDCl$_3$) δ=41.5, 61.1, 125.6, 126.7, 127.5, 127.6, 128.6, 128.9, 130.0, 130.3, 130.8, 131.3, 134.3, 141.8, 154.5, 166.3; MS(m/z)=326(M$^+$).

Example 2

Asymmetric Intramolecular Cyclization Reaction of N-acylhydrazone

An asymmetric intramolecular cyclization reaction of N-acylhydrazone obtained from α,β-unsaturated ketone was performed according to the following reaction formula (B).

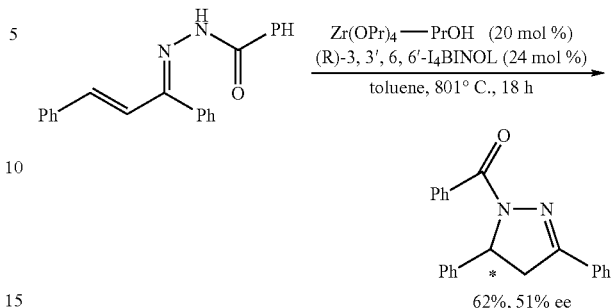

(B)

Under an atmosphere of argon, a solution of zirconium propoxide propanol complex (31 mg, purity: 77%) in toluene (0.4 ml) was added to a suspension of (R)-3,3',6,6'-tetraiodo-1,1'-binaphthalene-2,2'-diol (70 mg) in anhydrous toluene (0.3 ml). The resulting mixture was stirred at room temperature for 3 hours to afford a solution of a chiral zirconium catalyst. Anhydrous toluene (0.7 ml) was added to benzoylhydrazone derived from chalcone (121 mg) in another well dried glass vessel. The solution of zirconium catalyst was added to the suspension of hydrazone using anhydrous toluene (0.4 ml) through a cannula under an atmosphere of argon.

The resulting mixture was stirred at 80° C. for 18 hours. After cooling the reaction mixture to room temperature, the reaction was stopped by addition of saturated aqueous solution of sodium hydrogen carbonate to the reaction mixture. The resulting reaction mixture was separated and the water layer was extracted with methylene chloride. The organic layers were collected.

The organic layer was dried over anhydrous sodium sulfate, filtered and concentrated to afford a crude product. It was purified through silica gel thin layer chromatography to give 1-benzoyl-3,5-diphenyl-2-pyrazoline (76 mg, yield 62%) as a target product. The optical purity of the product was 51% ee.

The data for identification of the product is shown in Table 2.

TABLE 2

HPLC(Daicel CHIRALCEL OD, n-hexane: i-PrOH=9:1, 1.0 mL/min); t$_R$=21 min(minor), t$_R$=37 min(major).

Example 3

Asymmetric Intermolecular Cyclization Reaction of an N-acylhydrazone with an Olefinic Compound An asymmetric intermolecular cyclization reaction of an N-acylhydrazone with an olefinic compound was conducted according to the following reaction formula (C).

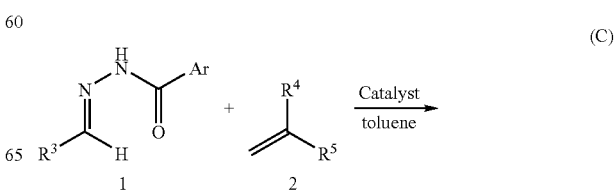

(C)

-continued

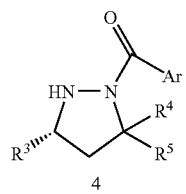

1a: $R^3$=PhCH$_2$CH$_2$, Ar=p-NO$_2$C$_6$H$_4$
1b: $R^3$=PhCH$_2$CH$_2$, Ar=Ph
1c: $R^3$=(CH$_3$)$_2$CHCH$_2$, Ar=Ph
1d: $R^3$=c-C$_6$H$_{11}$, Ar=Ph
1e: $R^3$=CH$_3$(CH$_2$)$_4$, Ar=Ph
1f: $R^3$=CH$_3$(CH$_2$)$_2$, Ar=Ph
1g: $R^3$=PhCH$_2$, Ar=Ph
1h: $R^3$=(CH$_3$)$_2$CHCH$_2$, Ar=p-NO$_2$C$_6$H$_4$
1i: $R^3$=c-C$_6$H$_{11}$, Ar=p-NO$_2$C$_6$H$_4$
1j: $R^3$=CH$_3$(CH$_2$)$_4$, Ar=p-NO$_2$C$_6$H$_4$
1k: $R^3$=Ph, Ar=o,p-(NO$_2$)$_2$C$_6$H$_3$
1l: $R^3$=PhSCH$_2$, Ar=p-NO$_2$C$_6$H$_4$
2a: $R^4$=$R^5$=SCH$_3$
2b: $R^4$=H, $R^5$=OCH$_2$CH$_3$
2c: $R^4$=H, $R^5$=OCH$_2$CH$_2$CH$_3$
2d: $R^4$=H, $R^5$=OC(CH$_3$)$_3$
2e: $R^4$=H, $R^5$=SCH$_2$CH$_3$
catalyst=Zr(OPr)$_4$+

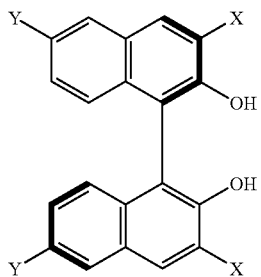

(R)-3a: X=Y=I
(R)-3b: X=I, Y=H
(R)-3c: X=Br, Y=H (1) Asymmetric Cyclization Reaction of Compound (1b) with (2a)

At room temperature, a solution of Zr(OPr)$_4$ (0.040 mmol) in toluene (0.4 ml) was added to a suspension of (R)-3,3'-I$_2$BINOL (3b) (0.048 mmol) in toluene (0.3 ml). The resulting mixture was stirred for 0.5 hours at the same temperature, and then a solution of propanol (0.2 mmol) in toluene (0.3 ml) was added to the mixture. The resulting mixture was further stirred for 0.5 hours.

The obtained catalyst solution was transferred to hydrazone (1b) (0.40 mmol) in another vessel using toluene (0.5 ml) through a cannula. This mixture was stirred at 0° C. to afford a suspension.

A solution of ketene acetal (2a) in toluene (0.5 ml) was added to the suspension and the resulting mixture was stirred for 18 hours at the same temperature.

The reaction was stopped by addition of water to the reaction mixture. The mixture was then extracted with CH$_2$Cl$_2$ three times. The organic layers were collected. The organic layer was dried over anhydrous Na$_2$SO$_4$, filtered and dried under reduced pressure to dryness to give a crude product. It was purified through column chromatography (aluminum oxide) to give a pyrazolidine derivative (4ba) as a target product. The optical purity of the product was determined by HPLC using a chiral column.

(2) Asymmetric Cyclization Reaction of Compound (1a) with (2c)

At room temperature, a solution of Zr(OPr)$_4$ (0.040 mmol) in toluene (0.4 ml) was added to a suspension of (R)-3,3',6,6'-I$_4$BINOL (3a) (0.048 mmol) in toluene (0.3 ml). The resulting mixture was stirred for 3 hours at the same temperature.

The obtained catalyst solution was transferred to hydrazone (1a) (0.4 mmol) in another vessel using toluene (0.8 ml) through a cannula. This mixture was stirred at 0° C.

A solution of vinyl ether (2c) (4.0 mmol) in toluene (0.5 ml) was added to the suspension and then the resulting mixture was stirred for 18 hours at the same temperature.

The reaction was stopped by addition of water to the reaction mixture. The mixture was then extracted with CH$_2$Cl$_2$ three times. The organic layers were collected. The organic layer was dried over anhydrous Na$_2$SO$_4$, filtered and dried under reduced pressure to give a crude product. It was purified through column chromatography (aluminum oxide) to give a target pyrazolidine derivative (4ac) as a mixture of diastereomers. The ratio of the diastereomers was obtained by $^1$H NMR spectrum of the mixture. The optical purity of the product was determined by HPLC using a chiral column.

Various kinds of the reactions of N-acylhydrazone derivatives (compounds 1a to 1l) with olefin compounds (2a to 2e) were conducted by similar methods. The data for identification of pyrazolidine derivatives (4ba, 4ca, 4da, 4ea, 4fa, 4ga, 4ab, 4ac, 4ad, 4ae, 4hc, 4ic, 4jc, 4kc and 4lc), as representative examples, are shown in Tables 3 to 18.

TABLE 3

1-(p-Nitrobenzoyl)-5,5-bis(methylthio)-3-(2-phenylethyl)
pyrazolidine(4aa): [α]$_D^{28}$?05.05(c 2.49, benzene, 63% ee);
IR[cm$^{-1}$] (neat) 3209, 1653, 1602, 1522, 1496, 1388, 1344, 1233; $^1$H
NMR(CDCl$_3$) δ=1.85(m, 2H), 2.18(dd, 1H, J=13.7, 7.8 Hz), 2.32(s,
3H), 2.41(s, 3H), 2.63(m, 2H), 2.82(dd, 1H, J=13.6, 7.1 Hz),
3.30(m, 1H), 4.58(br, 1H), 7.1(m, 2H), 7.2-7.4(m, 3H), 7.76(d, 2H,
J=9.0 Hz), 8.22(d, 2H, J=9.0 Hz); $^{13}$C NMR(CDCl$_3$) δ=15.8, 15.9,
32.8, 34.1, 51.5, 56.8, 82.4, 122.7, 126.2, 128.1, 128.4, 129.2, 140.5,
142.2, 148.2, 165.8; HPLC Daicel Chiralpak AD, hexane/$^i$PrOH=9/1,
flow rate=0.5 mL/min: $^t$R=57 min(minor), $^t$R=64 min(major).

TABLE 4

1-Benzoyl-5,5-bis(methylthio)-3-(2-phenylethyl)
pyrazolidine(4ba): [α]$_D^{22}$+1.89(c 1.03, benzene, 97% ee);
IR[cm$^{-1}$] (neat) 3207, 1739, 1637, 1602, 1577, 1496, 1444,
1383, 1244; $^1$H NMR(CDCl$_3$) δ=1.81(m,
1H), 1.90(m, 1H), 2.18(dd, 1H, J=13.6, 7.6 Hz), 2.31(s,
3H), 2.40(s, 3H), 2.6-2.7(m, 2H), 2.80(dd, 1H, J=13.6, 6.8 Hz),
3.31(m, 1H), 4.62(dbr, 1H, J=10.5 Hz), 7.12(d, 2H, J=7.1 Hz),
7.2(m, 1H), 7.3(m, 2H), 7.4(m, 3H), 7.67(d, 2H, J=6.6 Hz); $^{13}$C
NMR(CDCl$_3$) δ=15.8, 16.0, 32.9, 34.7, 51.8, 56.6, 82.4, 126.1, 127.4,
128.3, 128.5, 128.6, 130.1, 136.1, 140.9, 168.1; HPLC Daicel
Chiralcel OD, hexane/$^i$PrOH=9/1, flow rate=0.3 mL/min:
$^t$R=78 min(major), $^t$R=86 min(minor).

TABLE 5

1-Benzoyl-5,5-bis(methylthio)-3-(2-methylpropyl)
pyrazolidine(4ca): [α]$_D^{30}$+7.61(c 2.90, benzene, 96% ee);
IR[cm$^{-1}$] (neat) 3205, 1645, 1577, 1468, 1444, 1377, 1317,
1253, 1209; $^1$H NMR(CDCl$_3$) δ=0.89(d,
3H, J=6.6 Hz), 0.91(d, 3H, J=6.6 Hz), 1.31(ddd, 1H,

TABLE 5-continued

J=13.6, 6.8, 6.8 Hz), 1.45(ddd, 1H, J=13.6, 7.1, 7.1 Hz), 1.63(m, 1H), 2.09(dd, 1H, J=13.4, 8.3 Hz), 2.32(s, 3H), 2.40(s, 3H), 2.85(dd, 1H, J=13.4, 6.6 Hz), 3.40(m, 1H), 4.46(dbr, 1H, J=11.2 Hz), 7.3-7.4(m, 3H), 7.6-7.7(m, 2H); $^{13}$C NMR(CDCl$_3$) δ=15.8, 15.9, 22.5, 22.6, 25.8, 41.7, 52.2, 55.8, 82.1, 127.3, 128.5, 130.0, 136.1, 167.7; HPLC Daicel Chiralcel OD, hexane/$^i$PrOH=40/1, flow rate=1.0 mL/min: $^t$R=20 min(major), $^t$R=24 min(minor).

TABLE 6

1-Benzoyl-5,5-bis(methylthio)-3-cyclohexylpyrazolidine(4da): [α]$_D^{30}$+26.0(c 2.49, benzene, 95% ee); IR[cm$^{-1}$] (neat) 3191, 1613, 1600, 1577, 1508, 1445, 1409, 1376, 1290, 1251, 1206; $^1$H NMR(CDCl$_3$) δ=0.9-1.6(m, 6H), 1.6-1.8(m, 5H), 2.17(dd, 1H, J=13.4, 9.0 Hz), 2.31(s, 3H), 2.40(s, 3H), 2.79(dd, 1H, J=13.4, 6.8 Hz), 3.07(m, 1H), 4.48(d, 1H, J=11.6 Hz), 7.3-7.4(m, 3H), 7.67(m, 2H); $^{13}$C NMR(CDCl$_3$) δ=15.9, 16.0, 25.6, 25.8, 26.2, 29.6, 30.8, 40.8, 50.1, 62.6, 82.3, 127.3, 128.7, 130.1, 136.1, 167.7; HPLC Daicel Chiralcel OD, hexane/$^i$PrOH=40/1, flow rate=0.5 mL/min: $^t$R=42 min(major), $^t$R=51 min(minor).

TABLE 7

1-Benzoyl-5,5-bis(methylthio)-3-pentylpyrazolidine(4ea): [α]$_D^{24}$+8.12(c 1.47, benzene, 98% ee); IR[cm$^{-1}$] (neat) 3206, 1645, 1462, 1377; $^1$H NMR(CDCl$_3$) δ=0.88(t, 3H, J=6.8H), 1.3-1.5(m, 6H), 1.6-1.7(m, 2H), 2.13(dd, 1H, J=13.4, 8.1 Hz), 2.32(s, 3H), 2.41(s, 3H), 2.84(dd, 1H, J=13.4, 6.8 Hz), 3.32(m, 1H), 4.50(dbr, 1H, J=11.2 Hz), 7.3-7.4(m, 3H), 7.66(m, 2H); $^{13}$C NMR(CDCl$_3$) δ=13.9, 15.9, 16.0, 22.5, 26.4, 31.6, 32.8, 52.0, 57.6, 82.3, 127.4, 128.6, 130.1, 136.2, 167.9; HPLC Daicel Chiralcel OD, hexane/$^i$PrOH=40/1, flowrate=0.5 mL/min: $^t$R=47 min(major), $^t$R=52 min(minor).

TABLE 8

1-Benzoyl-5,5-bis(methylthio)-3-propylpyrazolidine(4fa): [α]$_D^{26}$+12.2(c 1.77, benzene, 96% ee); IR[cm$^{-1}$] (neat) 3205, 1645, 1577, 1441, 1376, 1251, 1211; $^1$H NMR(CDCl$_3$) δ=0.91(t, 3H, J=7.1 Hz), 1.4(m, 3H), 1.57(m, 1H), 2.12(dd, 1H, J=13.6, 8.4 Hz), 2.32(s, 3H), 2.40(s, 3H), 2.84(dd, 1H, J=13.6, 6.8 Hz), 3.33(m, 1H), 4.51(dbr, 1H, J=11.2 Hz), 7.3-7.4(m, 3H), 7.67(m, 2H); $^{13}$C NMR(CDCl$_3$) δ=13.8, 15.8, 15.9, 19.9, 34.7, 51.8, 57.2, 82.2, 127.3, 128.5, 130.0, 136.1, 167.8; HPLC Daicel Chiralpak AD, hexane/$^i$PrOH=40/1, flow rate=0.5 mL/min: $^t$R=50 min(minor), $^t$R=56 min(major).

TABLE 9

1-Benzoyl-5,5-bis(methylthio)-3-benzylpyrazolidine(4ga): [α]$_D^{27}$+5.46(c 2.84, benzene, 97% ee); IR[cm$^{-1}$] (neat) 3205, 1644, 1601, 1577, 1496, 1448, 1377, 1241; $^1$H NMR(CDCl$_3$) δ=2.26(s, 3H), 2.26(m, 1H), 2.36(s, 3H), 2.65(dd, 1H, J=13.7, 6.8 Hz), 2.69(dd, 1H, J=13.9, 7.6 Hz), 2.94(dd, 1H, J=13.9, 6.6 Hz), 3.59(m, 1H), 4.75(dbr, 1H, J=9.5 Hz), 7.10(d, 2H, J=6.6 Hz), 7.2-7.4(m, 6H), 7.67(m, 2H); $^{13}$C NMR(CDCl$_3$) δ=15.6, 15.8, 38.2, 50.5, 58.1, 82.2, 126.3, 127.1, 128.3, 128.4, 128.7, 129.8, 135.8, 137.3, 167.7; HPLC Daicel Chiralpak AD, hexane/$^i$PrOH=9/1, flow rate=1.0 mL/min: $^t$R=16 min(minor), $^t$R=21 min(major).

TABLE 10

1-(p-Nitrobenzoyl)-5-ethoxy-3-(2-phenylethyl)pyrazolidine(4ab): IR[cm$^{-1}$] (neat) 3254, 1647, 1602, 1523, 1496, 1476, 1350; $^1$H NMR(CDCl$_3$, two diastereomers mixture) δ=1.23(t, 3H, J=7.1 Hz), 1.3-1.5(m, 1H), 1.66(ddd, 0.5H, J=13.2, 9.5, 3.4 Hz), 1.8-1.9(m, 1H), 2.0-2.1(m, 0.5H), 2.21(ddd, 0.5H, J=13.7, 8.0, 2.7 Hz), 2.27(br, 1H), 2.5-2.7(m, 1.5H), 2.89(br, 0.5H), 3.37(br,

TABLE 10-continued 0.5H), 3.72(br, 2H), 4.03(dbr, 0.5H, J=12.0 Hz), 4.67(dbr, 0.5H, J=3.9 Hz), 5.95(br, 0.5H), 6.04(br, 0.5H), 6.86(dbr, 1H, J=6.8 Hz), 7.03(dbr, 1H, J=7.1 Hz), 7.1-7.2(m, 3H), 7.83(d, 1H, J=8.6 Hz), 7.91(d, 1H, J=8.8 Hz), 8.24(d, 1H, J=8.5 Hz), 8.25(d, 1H, J=8.5 Hz); $^{13}$C NMR(CDCl$_3$, two diastereomers mixture) δ=15.1, 15.1, 32.8, 32.9, 34.0, 35.8, 40.2, 41.2, 58.6, 60.3, 64.5, 64.8, 86.9, 87.7, 122.7, 125.9, 126.1, 128.1, 128.2, 128.3, 128.4, 129.9, 130.1, 140.6, 140.9, 141.0, 148.6, 169.4, 170.2; EI-HRMS(m/z) calcd. for C$_{20}$H$_{23}$N$_3$O$_4$(M$^+$): 369.1689; found: 369.1706; HPLC Daicel Chiralpak AD-H, hexane/$^i$PrOH=9/1, flow rate=0.3 mL/min: major diastereomer $^t$R=61 min(major), $^t$R=66 min(minor); minor diastereomer $^t$R=46 min(major), $^t$R=50 min(minor).

TABLE 11

1-(p-Nitrobenzoyl)-5-(1-propoxy)-3-(2-phenylethyl)pyrazolidine(4ac): IR[cm$^{-1}$](neat) 3255, 1641, 1600, 1523, 1344; $^1$H NMR(CDCl$_3$, two diastereomers mixture) δ=0.94(t, 3H, J=7.3 Hz), 1.3-1.5(m, 1H), 1.61(q, 2H, J=7.1 Hz), 1.66(m, 0.5H), 1.8-2.0(m, 1H), 2.0-2.1(m, 0.5H), 2.22(ddd, 0.5H, J=13.7, 8.1, 2.4 Hz), 2.28(br, 1H), 2.59(m, 0.5H), 2.63(m, 1H), 2.91(br, 0.5H), 3.62(br, 2H), 4.01(dbr, 0.5H, J=11.4 Hz), 4.65(br, 0.5H), 5.95(br, 0.5H), 6.03(br, 0.5H), 6.86(dbr, 0.5H, J=6.8 Hz), 7.04(dbr, 0.5H, J=6.8 Hz), 7.1-7.3(m, 3H), 7.83(d, 1H, J=8.8 Hz), 7.91(d, 1H, J=8.8 Hz), 8.25(d, 1H, J=8.8 Hz), 8.25(d, 1H, J=9.0 Hz); $^{13}$C NMR(CDCl$_3$, two diastereomers mixture) δ=10.6, 22.8, 22.9, 32.8, 32.9, 34.1, 35.8, 40.2, 41.2, 58.6, 60.3, 70.8, 71.0, 87.0, 87.9, 122.7, 126.0, 126.2, 128.2, 128.3, 128.4, 128.4, 129.9, 130.2, 140.6, 141.0, 141.0, 148.7, 169.4, 170.2; EI-HRMS(m/z) calcd. for C$_{21}$H$_{25}$N$_3$O$_4$(M$^+$): 383.1845; found: 383.1838; HPLC Daicel Chiralpak AD, hexane/$^i$PrOH=40/1, flow rate=0.8 mL/min: major diastereomer $^t$R=69 min(major), $^t$R=88 min(minor); minor diastereomer $^t$R=50 min(minor), $^t$R=54 min(major).

TABLE 12

1-(p-Nitrobenzoyl)-5-(tert-butoxy)-3-(2-phenylethyl)pyrazolidine(4ad): IR[cm$^{-1}$](neat) 3250, 1636, 1601, 1521, 1391, 1353, 1235; $^1$H NMR(CDCl$_3$, two diastereomers mixture) δ=1.31(s, 9H), 1.2-1.5(m, 1.8H), 1.64(ddd, 0.2H, J=13.4, 8.6, 3.0 Hz), 1.80(m, 0.2H), 1.91(ddd, 0.8H, J=13.4, 6.1, 3.7 Hz), 2.16(ddd, 0.8H, J=13.4, 8.1, 1.2 Hz), 2.26(t, 1.6H, J=7.6 Hz), 2.52(ddd, 0.2H, J=13.4, 7.3, 7.3 Hz), 2.60(t, 0.4H, J=7.8 Hz), 2.83(m, 0.2H), 3.36(m, 0.8H), 4.07(dbr, 0.2H, J=12.0 Hz), 4.74(dbr, 0.8H, J=5.4 Hz), 6.15(dbr, 0.2H, J=4.2 Hz), 6.25(dbr, 0.8H, J=5.9 Hz), 6.84(dbr, 1.6H, J=7.3 Hz), 7.01(dbr, 0.4H, J=6.8 Hz), 7.1-7.2(m, 3H), 7.80(d, 0.4H, J=8.6 Hz), 7.87(d, 1.6H, J=8.6 Hz), 8.22(d, 2H, J=8.8 Hz); $^{13}$C NMR(CDCl$_3$, two diastereomers mixture) δ=28.3, 28.4, 32.8, 32.8, 34.2, 36.4, 41.5, 42.7, 58.4, 60.1, 75.0, 75.1, 81.3, 81.9, 122.6, 125.8, 126.0, 128.1, 128.2, 128.2, 128.3, 129.8, 130.1, 140.7, 141.0, 141.2, 141.3, 148.5, 168.5, 169.1; EI-HRMS(m/z) calcd. for C$_{22}$H$_{27}$N$_3$O$_4$(M$^+$): 397.2002; found: 397.2006; HPLC Daicel Chiralpak AD, hexane/$^i$PrOH=40/1, flow rate=0.8 mL/min: major diastereomer $^t$R=41 min(major), $^t$R=47 min(minor); minor diastereomer $^t$R=26 min(major), $^t$R=32 min(minor).

TABLE 13

1-(p-Nitrobenzoyl)-5-ethylthio-3-(2-phenylethyl)pyrazolidine(4ae): IR[cm$^{-1}$](neat) 3251, 1643, 1601, 1521, 1496, 1453, 1349, 1219;; $^1$H NMR(CDCl$_3$, two diastereomers mixture) δ=1.33(t, 0.2H, J=7.3 Hz), 1.35(t, 0.8 Hz, J=7.6 Hz), 1.3-1.5(m, 2H), 1.84(m, 0.2H), 1.98(m, 0.8H), 2.23(m, 0.8H), 2.27(tbr, 1.6H, J=7.8 Hz), 2.6-2.8(m, 1.8H), 2.8-3.0(m, 1.2H), 3.29(m, 0.8 Hz), 4.24(dbr, 0.2H, J=12.4 Hz), 4.91(dbr, 0.8H, J=4.9 Hz), 5.93(dd, 0.2H, J=8.3, 5.6 Hz), 6.04(dd, 0.8H, J=8.0, 4.4 Hz), 6.86(d, 1.6H, J=7.1 Hz), 7.04(m, 0.4 Hz), 7.1-7.3(m, 3H), 7.83(d, 0.4H, J=8.8 Hz), 7.91(d, 1.6H, J=8.8 Hz), 8.2-8.3(m, 2H); $^{13}$C NMR(CDCl$_3$, two diastereomers mixture) δ=14.9, 26.1, 26.3, 32.7, 32.9, 33.9, 35.4, 39.8, 40.9, 58.5, 60.1, 60.3, 61.0, 122.7, 122.7, 125.9, 126.2, 128.1, 128.2, 128.3, 128.4, 129.9, 130.1, 140.4, 140.8, 140.8, 148.7, 168.5,

TABLE 13-continued 169.6; EI-HRMS(m/z) calcd. for $C_{20}H_{23}N_3O_3S(M^+)$: 385.1460; found: 385.1465; HPLC Daicel Chiralpak AD-H, hexane/$^i$PrOH=19/1, flow rate=0.8 mL/min: major diastereomer $^t$R=48 min(major), $^t$R=55 min(minor); minor diastereomer $^t$R=34 min(minor), $^t$R=41 min(major).

TABLE 14

1-(p-Nitrobenzoyl)-5-(1-propoxy)-3-(2-methylpropyl)pyrazolidine(4hc): IR[cm$^{-1}$](neat) 3252, 1645, 1602, 1523, 1471, 1345, 1314; $^1$H NMR(CDCl$_3$, two diastereomers mixture) δ=0.59(d, 1.6H, J=6.4 Hz), 0.70(d, 1.6H, J=6.3 Hz), 0.81(d, 1.4H, J=6.6 Hz), 0.82(d, 1.4H, J=6.6 Hz), 0.89(t, 3H, J=7.6 Hz), 0.98(m, 0.4H), 1.16(m, 0.6H), 1.3-1.5(m, 1H), 1.5-1.7(m, 2.4H), 1.95(m, 0.6H), 2.16(m, 0.6H), 2.57(ddd, 0.4H, J=13.4, 7.0, 7.0 Hz), 2.96(m, 0.4H), 3.43(br, 0.6H), 3.59(br, 2H), 3.95(dbr, 0.4H, J=12.0 Hz), 4.59(dbr, 0.6H, J=4.4 Hz), 5.92(br, 0.4H), 5.95(br, 0.6H), 7.83(d, 1H, J=8.8 Hz), 7.84(d, 1H, J=8.8 Hz), 8.19(dbr, 2H, J=8.0 Hz); $^{13}$C NMR(CDCl$_3$, two diastereomers mixture) δ=10.5, 21.6, 22.4, 22.7, 22.8, 22.8, 25.0, 26.1, 40.3, 41.5, 41.6, 43.1, 70.7, 70.9, 86.9, 87.8, 122.5, 122.6, 129.8, 129.9, 141.0, 141.2, 148.5, 148.5, 169.1, 170.2; EI-HRMS(m/z) calcd. for $C_{17}H_{25}N_3O_4(M^+)$: 335.1845; found: 335.1851; HPLC Daicel Chiralpak AS, hexane/$^i$PrOH=19/1, flow rate=0.5 mL/min: major diastereomer $^t$R=57 min(minor), $^t$R=68 min(major); minor diastereomer $^t$R=26 min(major), $^t$R=34 min(minor).

TABLE 15

1-(p-Nitrobenzoyl)-5-(1-propoxy)-3-cyclohexylpyrazolidine(4ic): IR[cm$^{-1}$](neat) 3259, 1645, 1601, 1523, 1473, 1344, 1315; $^1$H NMR(CDCl$_3$, two diastereomers mixture) δ=0.5?1.4(m, 10H), 1.4-1.8(m, 6.4H), 2.08(br, 1H). 2.49(ddd, 0.4H, J=13.4, 7.1, 7.1 Hz), 2.66(ddd, 0.4H, J=18.1, 8.5, 8.5 Hz), 3.01(br, 0.6H), 3.56(br, 2H), 4.01(dbr, 0.4H, J=12.5 Hz), 4.57(br, 0.6H), 5.91(br, 1H), 7.8-7.9(m, 2H), 8.1-8.2(m, 2H); $^{13}$C NMR(CDCl$_3$, two diastereomers mixture) δ=10.5, 22.7, 22.8, 25.4, 25.5, 25.6, 25.8, 26.0, 26.1, 29.3, 29.5, 30.4, 30.8, 37.0, 39.3, 40.8, 41.0, 64.2, 66.1, 70.5, 70.8, 86.9, 87.7, 122.4, 129.8, 129.9, 140.9, 141.3, 148.4, 148.4, 168.9, 169.7; EI-HRMS(m/z) calcd. for $C_{19}H_{27}N_3O_4(M^+)$: 361.2002; found: 361.2002; HPLC Daicel Chiralpak AD with guard column, hexane/$^i$PrOH=30/1, flow rate=0.5 mL/min: major diastereomer $^t$R=79 min(minor), $^t$R=91 min(major); minor diastereomer $^t$R=43 min(major), $^t$R=57 min(minor).

TABLE 16

1-(p-Nitrobenzoyl)-5-(1-propoxy)-3-pentylpyrazolidine(4jc): IR[cm$^{-1}$](neat) 3258, 1647, 1602, 1523, 1470, 1344; $^1$H NMR(CDCl$_3$, two diastereomers mixture) δ=0.72(br, 1.7H), 0.81(br, 1.3H), 0.89(t, 3H, J=7.3 Hz), 0.8-1.3(m, 6.4H), 1.41(m, 0.3H), 1.57(m, 2.7H), 1.98(m, 0.6H), 2.14(m, 0.6H), 2.56(ddd, 0.4H, J=13.9, 7.3, 7.3 Hz), 2.92(br, 0.4H), 3.31(br, 0.6H), 3.59(br, 2H), 3.98(dbr, 0.4H, J=11.7 Hz), 4.60(br, 0.6H), 5.95(br, 1H), 7.84(m, 2H), 8.19(d, 2H, J=8.8 Hz); $^{13}$C NMR(CDCl$_3$, two diastereomers mixture) δ=10.5, 13.7, 13.8, 22.3, 22.7, 22.8, 26.1, 26.2, 31.3, 31.5, 32.4, 34.1, 40.1,

TABLE 16-continued 41.1, 59.3, 61.1, 70.7, 70.9, 87.0, 87.8, 122.5, 122.6, 129.8, 129.9, 141.0, 141.2, 148.4, 148.5, 169.1, 170.1; EI-HRMS(m/z) calcd. for $C_{18}H_{27}N_3O_4(M^+)$: 349.2002; found: 349.2008; HPLC Daicel Chiralpak AD-H, hexane/$^i$PrOH=19/1, flow rate=0.3 mL/min: major diastereomer $^t$R=53 min(minor), $^t$R=56 min(major); minor diastereomer $^t$R=39 min(major), $^t$R=46 min(minor).

TABLE 17

1-(o, p-Dinitrobenzoyl)-5-(1-propoxy)-3-phenylpyrazolidine(4kc): IR[cm$^{-1}$](neat) 3253, 1666, 1603, 1537, 1489, 1456, 1349, 1249; $^1$H NMR(CDCl$_3$, two diastereomers mixture) δ=1.00(t, 3H, J=7.3 Hz), 1.70(tq, 2H, J=7.3, 7.3 Hz), 2.28(ddd, 0.5H, J=13.6, 7.8, 2.4 Hz), 2.51(ddd, 0.5H, J=13.9, 8.1, 2.0 Hz), 2.70(ddd, 0.5H, J=13.9, 5.6, 5.6 Hz), 2.93(ddd, 0.5H, J=13.4, 7.3, 7.3 Hz), 3.7-3.9(m, 2H), 4.0-4.2(m, 1H), 4.58(br, 0.5H), 4.90(br, 0.5H), 6.03(m, 1H), 6.83(d, 0.5H, J=8.6 Hz), 6.98(d, 1H, J=7.1 Hz), 7.2-7.4(m, 4H), 7.70(d, 1H, J=8.5 Hz), 8.20(dd, 0.5H, J=8.3, 1.7 Hz), 8.50(dd, 0.5H, J=8.6, 1.5 Hz), 8.86(sbr, 0.5H), 8.91(sbr, 0.5H); $^{13}$C NMR(CDCl$_3$, two diastereomers mixture) δ=10.6, 10.6, 22.8, 22.9, 39.8, 41.7, 61.1, 63.6, 71.2, 71.2, 86.9, 87.6, 119.1, 119.3, 127.0, 127.4, 127.5, 127.7, 128.1, 128.4, 128.5, 128.8, 130.0, 130.1, 137.4, 138.2, 138.7, 139.7, 145.7, 145.9, 147.4, 147.7, 166.3, 166.7; EI-HRMS(m/z) calcd. for $C_{19}H_{20}N_4O_6(M^+)$: 400.1383; found: 400.1392; HPLC Daicel Chiralcel OD, hexane/$^i$PrOH=19/1, flow rate=1.0 mL/min: diastereomer A $^t$R=30 min(major), $^t$R=40 min(minor); diastereomer B $^t$R=48 min(minor), $^t$R=74 min(major).

TABLE 18

1-(p-Nitrobenzoyl)-5-(1-propoxy)-3-(phenylthiomethyl)pyrazolidine(4lc): IR[cm$^{-1}$](neat) 3252, 1651, 1601, 1523, 1494, 1479, 1439, 1345, 1315; $^1$H NMR(CDCl$_3$, two diastereomers mixture) δ=0.93(t, 1.8H, J=7.6 Hz), 0.94(t, 1.2H, J=7.3 Hz), 1.61(m, 2H), 1.89(m, 0.4H), 2.27(tbr, 1.2H, J=4.4 Hz), 2.5-2.7(m, 1H), 2.78(m, 0.6H), 3.11(m, 0.6H), 3.24(br, 0.4H), 3.5-3.7(m, 2.6H), 4.30(br, 0.4H), 4.83(br, 0.6H), 5.95(br, 0.4H), 6.04(br, 0.6H), 7.1-7.4(m, 5H), 7.82(d, 0.8H, J=8.5 Hz), 7.89(d, 1.2H, J=8.6 Hz), 8.2-8.3(m, 2H); $^{13}$C NMR(CDCl$_3$, two diastereomers mixture) δ=10.5, 10.6, 22.8, 22.8, 35.9, 38.4, 39.0, 39.9, 58.4, 59.8, 70.7, 70.9, 87.0, 87.6, 122.7, 122.8, 126.6, 127.0, 129.0, 129.0, 129.8, 130.0, 130.0, 130.3, 134.9, 135.2, 140.6, 148.7, 148.7, 169.0, 169.6; EI-HRMS(m/z) calcd. for $C_{20}H_{23}N_3O_4S(M^+)$: 401.1409; found: 401.1408; HPLC Daicel Chiralpak AD-H, hexane/$^i$PrOH=30/1, flow rate=1.0 mL/min: major diastereomer $^t$R=94 min(minor), $^t$R=108 min(major); minor diastereomer $^t$R=63 min(minor), $^t$R=67 min(major).

Table 19 shows the yields, diastereomer ratios, and optical purities of the products (4ba to 4kc). The reactions were carried out at 0° C. for 18 hours in the presence of an asymmetric zirconium catalyst (10 mol %) and propanol (50 mol %), unless otherwise noted. The asymmetric zirconium catalyst could be obtained by mixing Zr(OPr)$_4$ (10 mol %) and (R)-3 (12 mol %). The yield is an isolated yield. The ratios of diastereomers were evaluated by $^1$H NMR spectra.

TABLE 19

| Reaction | Hydrazone 1 | Olefin 2 | BINOL 3 | Product | Yield (%) | Diastereomer Ratio | ee % (major/minor) |
|---|---|---|---|---|---|---|---|
| 1 | 1b | 2a | 3b | 4ba | 87 | — | 97 |
| 2 | 1c | 2a | 3b | 4ca | 84 | — | 98 |
| 3 | 1d | 2a | 3b | 4da | 74 | — | 95 |
| 4* | 1e | 2a | 3b | 4ea | 79 | — | 97 |
| 5* | 1f | 2a | 3b | 4fa | 60 | — | 96 |
| 6 | 1g | 2a | 3b | 4ga | 90 | — | 97 |
| 7* | 1a | 2b | 3a | 4ab | 91 | 52/48 | 92/98 |

TABLE 19-continued

| Reaction | Hydrazone 1 | Olefin 2 | BINOL 3 | Product | Yield (%) | Diastereomer Ratio | ee % (major/minor) |
|---|---|---|---|---|---|---|---|
| 8* | 1a | 2c | 3a | 4ac | 95 | 54/46 | 92/98 |
| 9* | 1a | 2d | 3a | 4ad | 90 | 81/19 | 87/93 |
| 10* | 1a | 2e | 3a | 4ae | 38 | 76/24 | 92/92 |
| 11* | 1h | 2c | 3a | 4hc | 86 | 58/42 | 99/99 |
| 12* | 1i | 2c | 3a | 4ic | 95 | 67/33 | 92/99 |
| 13* | 1j | 2c | 3a | 4jc | 65 | 59/41 | 93/96 |
| 14*# | 1k | 2c | 3c | 4kc | 70 | 50/50 | 42/81 |

*Without propanol
Reaction condition: at 20° C. for 24 hours in the presence of zirconium catalyst obtained by mixing Zr(O$^t$Bu)$_4$ (20 mol %) and (R)-3c (24 mol %)

Example 4

A reaction of a compound (R$^3$=$^t$BuMe$_2$SiOCH$_2$CH$_2$, Ar=Ph) was carried out without addition of additional propanol according to Example 3 (1), which is a process for producing pyrazolidine derivative (4ba). A target pyrazolidine derivative having 97% ee optical purity in 77% yield was obtained. Reactions were performed in the same manner using 1.2 and 1.5 equivalents of ketene acetal (2a) instead of 2 equivalents of ketene acetal (2a) pyrazolidine derivative in 71% yield and 97% ee; and 85% yield and 97% ee, respectively was obtained.

Reference Example

Conversion of Pyrazolidine Derivatives (1) Synthesis of N-(3-amino-1-(methylthio)-5-phenylpentyl)benzamide (Compound 5)

Compound (4ba) (464 mg, 1.25 mmol) obtained in Example 3 was dissolved in methanol (MeOH) (35 ml) degassed fully. A solution of SmI$_2$ in THF solution (0.15 M, 50 ml, 7.5 mmol) was added to the solution of compound (4ba) at −78° C. and the resulting mixture was stirred for 14.5 hours at the same temperature.

The solution of the reaction mixture turned from dark green to yellow on exposure to air at −78° C. The solvent of the reaction mixture was evaporated and then the residue was dissolved in a mixture of solvents of CH$_2$Cl$_2$/NaHCO$_3$. This mixture was filtered through Celite (registered trademark) and the organic layer was collected. The water layer was washed with CH$_2$Cl$_2$ and the organic layers were collected. The organic layer was washed with water, and aqueous solution of sodium chloride, dried over anhydrous Na$_2$SO$_4$, filtered and concentrated under reduced pressure to afford a crude product. It was purified through column chromatography (silica gel, CHCl$_3$: MeOH=20:1) to give a product (320 mg, 78%) as a mixture of diastereomers.

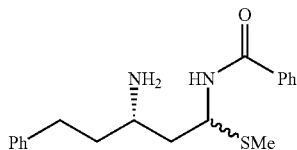

5

The data for identification of the obtained compound (5) are shown in Table 20.

TABLE 20

IR[cm$^{-1}$](neat) diastereomer A 3285, 1640, 1603, 1578, 1533, 1489, 1454, 1342; diastereomer B 3291, 1639, 1603, 1578, 1528, 1489, 1454, 1330; $^1$H NMR(CDCl$_3$) diastereomer A δ=1.65(m, 1H), 1.7-1.8(m, 2H), 1.98(ddd, 1H, J=14.4, 6.4, 2.4 Hz), 2.21(s, 3H), 2.6-2.8(m, 2H), 3.19(mbr, 1H), 5.60(ddd, 1H, J=9.0, 6.3, 3.6 Hz), 7.2-7.4(m, 3H), 7.27(m, 2H), 7.42(m, 2H), 7.49(m, 1H), 7.82(d, 2H, J=7.6 Hz), 8.81(dbr, 1H, J=8.8 Hz); diastereomer B δ=1.65(m, 1H), 1.8-1.9(m, 2H), 1.98(m, 1H), 2.17(s, 3H), 2.6-2.8(m, 2H), 2.62(ddd, 1H, J=13.7, 9.8, 6.4 Hz), 2.73(ddd, 1H, J=13.6, 10.0, 5.6 Hz), 2.95(m, 1H), 5.46(ddbr, 1H, J=15.4, 7.8 Hz), 7.1-7.2(m, 3H), 7.24(m, 2H), 7.30(dbr, 1H, J=7.6 Hz), 7.43(m, 2H), 7.51(m, 1H), 7.82(d, 2H, J=8.0 Hz); $^{13}$C NMR(CDCl$_3$) diastereomer A δ=14.4, 32.3, 41.5, 41.7, 48.8, 55.3, 125.9, 127.0, 128.2, 128.4, 128.4, 131.5, 133.9, 141.5, 166.3; diastereomer B δ=13.8, 32.2, 40.0, 42.8, 49.1, 54.3, 63.6, 125.9, 127.0, 127.3, 128.2, 128.4, 128.5, 131.7, 133.8, 141.5, 166.8; EI-HRMS(m/z) calcd. for C$_{19}$H$_{24}$N$_2$OS(M$^+$): 328.1609; diastereomer A, found: 328.1613; diastereomer B, found: 328.1609.

(2) Synthesis of N-Benzyl-N-(3-acetamido-5-phenylpentyl)acetamide (Compound 6)

Compound (5) (17.7 mg, 0.0539 mmol) resulting from the example (1) was added to a suspension of LiAlH$_4$ (31 mg, 0.817 mmol) in THF (1 ml) at room temperature and the mixture was heated under reflux for 6 hours. After cooling the reaction mixture to room temperature, to the reaction mixture was added successively water (0.03 ml), 15% aqueous solution of NaOH (0.03 ml) and water (0.09 ml) and then the resulting mixture was filtered through Celite (registered trademark). The Celite and recovered solid was well washed with CH$_2$Cl$_2$.

The filtrate was concentrated under reduced pressure and the residue was treated with an excess of acetic anhydride in pyridine at room temperature. The reaction was stopped by addition of saturated aqueous solution of NaHCO$_3$ and then CH$_2$Cl$_2$ was added to the mixture. The organic layer was separated and the water layer was extracted with CH$_2$Cl$_2$ and then the organic layers were collected. The organic layer was dried over anhydrous Na$_2$SO$_4$. A crude product was purified by thin later chromatography (silica gel, CHCl$_3$:EtOH=20:1) to give compound (6) (18 mg, 95%).

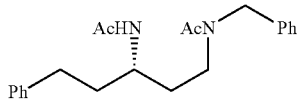

6

The data for identification of compound (6) are shown in Table 21.

TABLE 21

IR[cm$^{-1}$](neat) 3289, 1643, 1552, 1496, 1453, 1374, 1291; $^1$H NMR(CDCl$_3$, two rotamers mixture) δ=1.5-1.8(m, 4H), 1.89(s, 0.7H), 1.95(s, 2.3H), 2.11(s, 2.3H), 2.14(s, 0.7H), 2.60(m, 2H), 3.2(m, 1.3H), 3.58(m, 0.7H), 3.90(m, 1H), 4.48(d, 0.7H, J=16.8 Hz), 4.53(d, 0.7H, J=16.8 Hz), 4.54(d, 0.35H, J=14.9 Hz), 4.60(d, 0.35H, J=14.9 Hz), 5.18(br, 0.3H), 5.90(dbr, 0.7H, J=8.3 Hz), 7.1-7.4(m, 10H); $^{13}$C NMR(CDCl$_3$, two rotamers mixture) δ=21.4, 21.8, 23.3, 23.4, 32.3, 32.4, 34.6, 36.8, 36.9, 43.1, 45.2, 47.4, 47.5, 48.4, 52.5, 125.9, 126.1, 126.3, 127.4, 127.7, 128.1, 128.2, 128.3, 128.4, 128.6, 128.6, 129.0, 136.5, 137.6, 141.2, 141.7, 169.8, 170.0, 170.4, 171.2; EI-HRMS(m/z) calcd. for C$_{22}$H$_{28}$N$_2$O$_2$ (M$^+$): 352.2151; found: 352.2154.

(3) Synthesis of 1-Acetyl-5-(2-phenylethyl)-2-pyrazoline (Compound 7)

Compound (4ac) (105 mg, 0.274 mmol) was added to a suspension of LiAlH$_4$ (12.7 mg, 0.335 mmol) in THF (0.5 ml) at −78° C. and the mixture was stirred for 9 hours at the same temperature. The reaction was stopped by adding successively water (0.015 ml), 15% aqueous solution of NaOH (0.03 ml) and water (0.09 ml) to the reaction mixture.

After warming the reaction mixture to room temperature, anhydrous Na$_2$SO$_4$ was added to it and stirred for 5 minutes. The mixture was filtered through Celite (registered trademark). The Celite and recovered solid was satisfactorily washed with CH$_2$Cl$_2$. The filtrate was concentrated under reduced pressure to give a crude product. It was treated with a solution of acetyl chloride (195 μl, 2.74 mmol), pyridine (217 mg, 2.74 mmol) and dimethylaminopyridine (DMAP, 6.7 mg, 0.052 mmol) in CH$_2$Cl$_2$ (2 ml) between 0° C. and room temperature.

To this reaction mixture was added saturated aqueous solution of NaHCO$_3$ and the organic layer was removed. The water layer was extracted with CH$_2$Cl$_2$ and the organic layers were collected. The organic layer was dried over anhydrous Na$_2$SO$_4$. A crude product was purified by thin layer chromatography (silica gel, hexane:ethyl acetate=1:1 and then CHCl$_3$:ethyl acetate=4:1) to give the title compound (7) (45.2 mg, 76%, 95% ee).

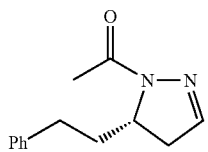

7

The data for identification are shown in Table 22.

TABLE 22

[α]$_D^{28}$+227(c 0.564, CDCl$_3$, 95% ee); IR[cm$^{-1}$] (neat) 1658, 1600, 1496, 1413, 1357, 1282; $^1$H NMR(CDCl$_3$) δ=1.84(m, 1H), 2.27(s, 3H), 2.30(m, 1H), 2.5-2.7(m, 3H), 3.02(ddd, 1H, J=18.7, 11.2, 1.7 Hz), 4.46(m, 1H), 6.85(tbr, 1H, J=1.7 Hz), 7.1-7.3(m, 5H); $^{13}$C NMR(CDCl$_3$)? ?=22.0, 31.0, 34.4, 39.3, 54.4, 126.0, 128.3, 128.4, 140.9, 146.3, 169.2; EI-HRMS(m/z) calcd. for C$_{13}$H$_{16}$N$_2$O(M$^+$): 216.1263; found: 216.1257; HPLC Daicel Chiralpak AD, hexane/$^i$PrOH=40/1, flow rate=1.0 mL/min: $^t$R=20 min(major), $^t$R=26 min(minor).

(4) Synthesis of S-ethyl (5-(2-phenylethyl)-2-(p-nitrobenzoyl) pyrazolidin-3-yl)ethanethioate (Compound 8)

A solution of Me$_3$SiOTf (100.1 mg, 0.450 mmol) in CH$_3$CN (0.2 ml) was added to a solution of compound (4ac) (58.2 mg, 0.152 mmol) and trimetylsilylenolether of S-ethyl ethanethioate (79.3 mg, 0.450 mmol) in CH$_3$CN (0.5 ml) at 0° C. and the mixture was stirred for 24 hours at the same temperature. After the reaction was stopped by addition of water, CH$_2$Cl$_2$ was added to the reaction mixture. The organic layer was removed and the water layer was extracted with CH$_2$Cl$_2$. The organic layers were collected. The organic layer was dried over anhydrous Na$_2$SO$_4$, filtered, and concentrated under reduced pressure to afford a crude product. It was purified by thin layer chromatography (hexane:ethyl acetate=3:1) to give the title compound (8) (44.2 mg, 68%, dr=86/14).

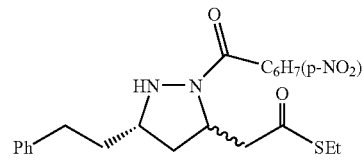

8

The data for identification are shown in Table 23.

TABLE 23

IR[cm$^{-1}$] (neat) 3248, 1684, 1627, 1599, 1523, 1497, 1454, 1413, 1350, 1265, 1228; $^1$H NMR(CDCl$_3$, two diastereomers mixture)δ=1.26(t, 3H, J=7.6 Hz), 1.4-1.5(m, 1.6H), 1.6-1.7(m, 0.1H), 1.7-1.9(m, 0.2H), 2.1-2.2(m, 1.6H), 2.3-2.4(m, 1.6H), 2.52(m, 0.1H), 2.65(t, 0.2H, J=7.6 Hz), 2.90(q, 2H, J=7.6 Hz), 3.1-3.2(m, 1.8H), 3.2-3.3(m, 0.8H), 4.19(dbr, 0.1H, J=13.2 Hz), 4.72(m, 1.9H), 6.94(d, 1.8H, J=7.6 Hz), 7.08(d, 0.2H, J=7.6 Hz), 7.1-7.3(m, 3H), 7.82(d, 0.2H, J=8.6 Hz), 7.87(d, 1.8H, J=8.6 Hz), 8.2-8.3(m, 2H); $^{13}$C NMR(CDCl$_3$, two diastereomers mixture)δ=14.6, 14.6, 23.5, 32.7, 32.9, 33.3, 34.0, 37.7, 39.0, 45.9, 46.0, 53.8, 55.5, 58.7, 60.2, 122.7, 122.7, 125.9, 126.1, 128.2, 128.3, 128.4, 129.7, 129.8, 140.7, 141.0, 141.4, 141.6, 148.4, 167.5, 168.7, 197.8, 198.0; EI-HRMS(m/z) calcd. for C$_{22}$H$_{25}$N$_3$O$_4$S(M$^+$): 427.1566; found: 427.1548.

(5) Synthesis of 1-Nicotinoyl-5-phenylthiomethyl-2-pyrazoline (Compound 9)

A solution of compound (4lc) (617 mg, 1.54 mmol) in THF (2 ml) was added to a suspension of LiAlH$_4$ (118 mg, 3.11 mmol) in THF (2 ml) at −78° C. and the resulting mixture was stirred for 16 hours at the same temperature. The reaction was stopped by adding successively water (0.12 ml), 15% aqueous solution of NaOH (0.12 ml) and water (0.36 ml). After warming the reaction mixture up to room temperature, anhydrous Na$_2$SO$_4$ was added to the resulting mixture and this mixture was stirred for 5 minutes. The mixture was filtered through Celite (registered trademark) and then the Celite and recovered solid was well washed with CH$_2$Cl$_2$.

The filtrate was concentrated under reduced pressure to afford a residue. It was treated with a solution of nicotinoyl chloride hydrochloride (1.10 g, 6.15 mmol), $^i$Pr$_2$NEt (1.59 g, 12.3 mmol) and p-dimethylaminopyridine (DMAP, 187 mg, 1.53 mmol) in CH$_2$Cl$_2$ (2 ml) at 0° C. to room temperature.

Saturated aqueous solution of NaHCO₃ was added to the reaction mixture and the organic layer was removed. The water layer was extracted with CH₂Cl₂ and the organic layers were collected. The organic layer was dried over anhydrous Na₂SO₄. A crude product was purified through column chromatography (silica gel, hexane:ethyl acetate=1:2) to give the title compound (9) (312 mg, 68%).

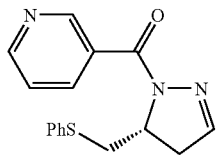

9

TABLE 24

IR[cm⁻¹] (neat) 1635, 1604, 1587, 1481, 1435, 1338, 1284, 1257; ¹H NMR(CDCl₃)δ=2.99(ddd, 1H, J=18.8, 5.1, 1.7 Hz), 3.11(ddd, 1H, J=18.8, 10.8, 1.4 Hz), 3.19(dd, 1H, J=14.1, 8.3 Hz), 3.62(dd, 1H, J=13.9, 2.7 Hz), 4.86(m, 1H), 6.97(sbr, 1H), 7.16(t, 1H, J=7.3 Hz), 7.2-7.3(m, 3H), 7.47(d, 2H, J=7.2 Hz), 7.99(ddd, 1H, J=8.0, 1.7, 1.7 Hz), 8.64(dd, 1H, J=4.9, 1.5 Hz), 8.92(d, 1H, J=1, 4 Hz); ¹³C NMR(CDCl₃)δ=34.8, 38.6, 54.9, 122.4, 126.3, 129.0, 129.9, 134.5, 137.0, 148.0, 150.5, 151.3, 165.0; EI-HRMS(m/z) calcd. for C₁₆H₁₅N₃OS(M⁺): 297.0936; found: 297.0945.

(6) Synthesis of (S)-5-Methyl-1-nicotinoyl-2-pyrazoline (ent MS-153, Compound 10)

Compound (9) (47.4 mg, 0.189 mmol) was dissolved in a suspension of Raney Ni (W-2, ca. 0.5 g) in a mixture of solvents (ethanol:acetic acid buffer solution (pH=5.2) (2:1)). The resulting mixture was stirred under an atmosphere of hydrogen (1 atm) for 64 hours. The reaction mixture was filtered through Celite (registered trademark) and then the recovered solid was sufficiently washed with EtOH.

The filtrate was concentrated under reduced pressure to afford a residue. It was dissolved in CH₂Cl₂ and the organic layer was washed with saturated aqueous solution of NaHCO₃, dried over anhydrous Na₂SO₄, filtered, and concentrated under reduced pressure to afford a crude product. It was purified by thin layer chromatography (silica gel, ethyl acetate) to give the title compound (10) (8.6 mg, 29%, 88% ee).

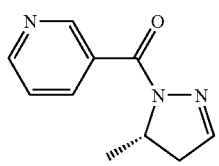

10

The data for identification are shown in Table 25

TABLE 25

[α]_D²⁵?345(c 0.5, EtOH, R-form); IR[cm⁻¹] (neat) 1639, 1593, 1570, 1479, 1435, 1336, 1284, 1255; ¹H NMR(CDCl₃) δ=1.42(d, 3H, J=6.6 Hz), 2.54(ddd, 1H, J=18.6, 4.9, 2.0 Hz), 3.14(ddd, 1H, J=18.6, 10.7, 1.7 Hz), 4.69(m, 1H), 6.93(dd, 1H, J=2.0, 1.7 Hz), 7.31(ddd, 1H, J=8.0, 4.9, 0.8 Hz), 8.10(ddd, J=8.0, 2.0, 2.0 Hz), 8.63(dd, 1H, J=4.9, 1.5 Hz), 9.02(d, 1H, J=1.7 Hz); ¹³C NMR(CDCl₃) δ=19.8, 41.3, 51.5, 122.5, 130.6, 137.0, 147.8, 150.6, 151.2, 164.8; EI-HRMS(m/z) calcd. for C₁₀H₁₁N₃O(M⁺): 189.0902; found: 189.0909;

TABLE 25-continued

HPLC Daicel Chiralcel OD, hexane/ⁱPrOH=9/1, flow rate=1.0 mL/min: ᵗR=27 min(R), ᵗR=31 min(S).

INDUSTRIAL APPLICABILITY

As described above in detail, the present invention provides a process for a reaction of intramolecular cyclization, asymmetric intramolecular cyclization and asymmetric intermolecular cyclization of an N-acylhydrazone, wherein a reaction is carried out under a mild condition such as in an organic solvent and at room temperature to a temperature of reflux and the like to give a pyrazoline and pyrazolidine skeleton with high stereoselectivity and in high yield.

In the first and second inventions indicated above, each a process for a reaction of intramolecular cyclization of an N-acylhydrazone, an N-acylhydrazone (I) described above is heated in the presence of a Lewis acid and then an intramolecular [3+2] additive cyclization reaction takes place to give an N-acylpyrazoline derivative (II) mentioned hereinbefore.

The third invention described above is a process for a reaction of asymmetric intramolecular cyclization of an N-acylhydrazone (I) described hereinbefore, wherein an N-acylhydrazone (I) is heated in the presence of an asymmetric Lewis acid catalyst obtained by mixing a zirconium alkoxide or zirconium dialkoxide dihalide and a binaphthol derivative, and then an intramolecular cyclization reaction takes place to give an optically active N-acylpyrazoline derivative.

The forth invention described above is a process for a reaction of asymmetric intermolecular cyclization of an N-acylhydrazone (V) described hereinbefore, wherein an N-acylhydrazone (V) is subjected to a reaction with an olefinic compound in the presence of an asymmetric Lewis acid catalyst obtained by mixing a zirconium alkoxide or zirconium dialkoxide dihalide and a binaphthol derivative, to give an optically active N-acylpyrazolidine derivative with high stereoselectivity.

The invention claimed is:

1. A process for intramolecular cyclization of an N-acylhydrazone which comprises reacting an N-acylhydrazone represented by the following formula (I)

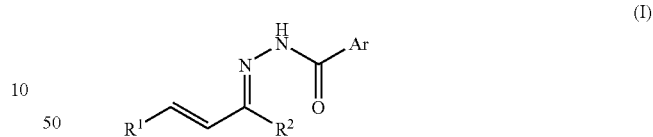

(I)

wherein R¹ and R² are the same or different and each represents a hydrogen atom or a hydrocarbon group, and Ar represents an optionally substituted aromatic hydrocarbon group, with a Lewis acid catalyst to obtain an N-acylpyrazoline derivative represented by the following formula (II)

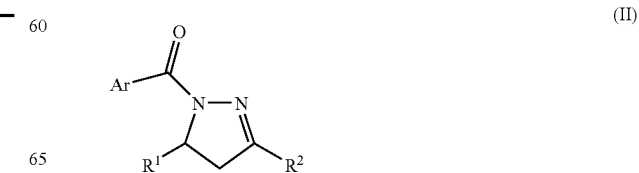

(II)

wherein $R^1$, $R^2$ and Ar have the same meanings as indicated above.

2. A process according to claim 1 wherein the Lewis acid catalyst is scandium triflate.

3. A process for asymmetric intramolecular cyclization of an N-acylhydrazone which comprises reacting an N-acylhydrazone represented by the following formula (I)

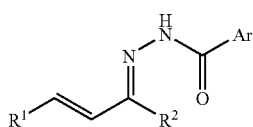
(I)

wherein $R^1$ and $R^2$ are the same or different and each represents a hydrogen atom or a hydrocarbon group, and Ar represents an optionally substituted aromatic hydrocarbon group, with an asymmetric Lewis acid catalyst, which can be obtained by mixing a zirconium alkoxide or zirconium dialkoxide dihalide represented by the following formula (III)

(III)

wherein P represents an alkoxy group, and Q represents an alkoxy group or a halogen atom, and a binaphthol derivative represented by the following formula (IV)

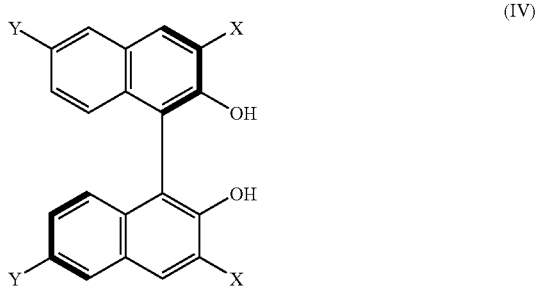
(IV)

wherein X represents a hydrogen atom, a halogen atom, a hydrocarbon group or a perfluoroalkyl group; Y represents a hydrogen atom, a halogen atom, a hydrocarbon group or a perfluoroalkyl group; and X and Y may be the same, to obtain an optically active N-acylpyrazoline derivative represented by the following formula (II')

(II')

wherein $R^1$, $R^2$ and Ar have the same meanings as indicated above.

4. A process for asymmetric intermolecular cyclization of an N-acylhydrazone which comprises reacting an N-acylhydrazone represented by the following formula (V)

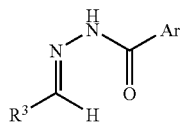
(V)

wherein $R^3$ represents an optionally substituted hydrocarbon group and Ar represents an optionally substituted aromatic hydrocarbon group, with an olefinic compound represented by the following formula (VI)

(VI)

wherein $R^4$ and $R^5$ are the same or different and each represents a hydrogen atom or a substituent selected from the group consisting of hydrocarbon group, alkoxy group and alkylthio group and at least one of $R^4$ and $R^5$ is other than a hydrogen atom, in the presence of an asymmetric Lewis acid catalyst, obtained by mixing a zirconium alkoxide or zirconium dialkoxide dihalide represented by the following formula (III)

(III)

wherein P represents an alkoxy group and Q represents an alkoxy group or a halogen atom, and a binaphthol derivative represented by the following formula (IV)

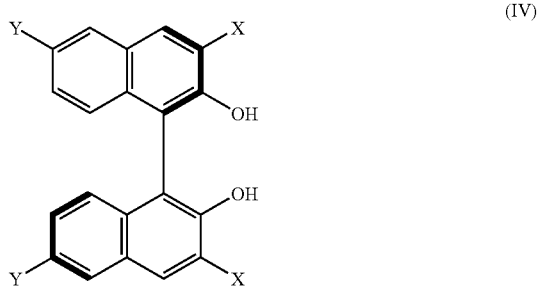
(IV)

wherein X represents a hydrogen atom, a halogen atom, a hydrocarbon group or a perfluoroalkyl group, and Y represents a hydrogen atom, a halogen atom, a hydrocarbon group or a perfluoroalkyl group and X and Y may be the same, to obtain an optically active N-acylpyrazolidine derivative represented by the following formula (VII)

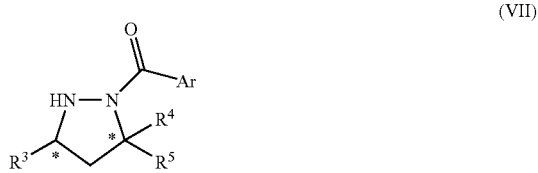
(VII)

wherein $R^3$ to $R^5$ and Ar have the same meanings as indicated above.

* * * * *